United States Patent
Kusuda et al.

(10) Patent No.: US 10,925,906 B2
(45) Date of Patent: Feb. 23, 2021

(54) COMPOSITION FOR IMPROVING BRAIN FUNCTION FOR NEONATES

(71) Applicant: Meiji Co., Ltd., Tokyo (JP)

(72) Inventors: Satoshi Kusuda, Tokyo (JP); Satsuki Totsu, Tokyo (JP); Masaki Terahara, Odawara (JP)

(73) Assignee: Meiji Co., Ltd.

( * ) Notice: Subject to any disclaimer, the term of this patent is extended or adjusted under 35 U.S.C. 154(b) by 0 days.

(21) Appl. No.: 16/092,778

(22) PCT Filed: Apr. 12, 2017

(86) PCT No.: PCT/JP2017/014915
§ 371 (c)(1),
(2) Date: Oct. 11, 2018

(87) PCT Pub. No.: WO2017/179602
PCT Pub. Date: Oct. 19, 2017

(65) Prior Publication Data
US 2019/0134114 A1    May 9, 2019

(30) Foreign Application Priority Data

Apr. 13, 2016 (JP) .............................. JP2016-080676

(51) Int. Cl.
*A61K 35/745* (2015.01)
*A61K 39/05* (2006.01)
*A23L 33/135* (2016.01)
*A23L 33/00* (2016.01)

(52) U.S. Cl.
CPC .......... *A61K 35/745* (2013.01); *A23L 33/135* (2016.08); *A23L 33/40* (2016.08); *A61K 39/05* (2013.01); *A23V 2002/00* (2013.01); *A23Y 2300/25* (2013.01)

(58) Field of Classification Search
CPC ...... A61K 35/745; A61K 35/74; A61K 47/36; A61K 35/744; A61K 9/0053; A61K 9/0095; A23L 33/135; A23L 33/40; A23V 2002/00; A23V 2200/304; A23V 2250/5114; A23Y 2300/25; A61P 37/08; C12N 1/20
See application file for complete search history.

(56) References Cited

U.S. PATENT DOCUMENTS

| 6,284,243 | B1 | 9/2001 | Masuyama et al. |
| 2002/0031507 | A1 | 3/2002 | De Simone |
| 2009/0142374 | A1* | 6/2009 | Moro ................... A61K 35/745 424/234.1 |
| 2011/0280837 | A1 | 11/2011 | Bergonzelli et al. |
| 2012/0009163 | A1 | 1/2012 | Sawada et al. |
| 2014/0271562 | A1 | 9/2014 | Garcia-Rodenas et al. |
| 2014/0363410 | A1 | 12/2014 | Bergonzelli Degonda et al. |
| 2015/0366919 | A1* | 12/2015 | Garssen ................. A23L 33/21 424/93.4 |
| 2016/0050960 | A1 | 2/2016 | Van Den Braak et al. |

FOREIGN PATENT DOCUMENTS

| JP | 2003501339 A | 1/2003 |
| JP | 2011517568 A | 6/2011 |
| JP | 5273695 B2 | 8/2013 |
| JP | 2015503913 A | 2/2015 |
| WO | 2008081934 A1 | 7/2008 |
| WO | 2013057049 A1 | 4/2013 |
| WO | 2014148887 A1 | 9/2014 |

OTHER PUBLICATIONS

Furuya et al, "Current Trend and Perspective on the Prevention of Disease by Oral Administration of Sphingolipids, and Utilization of Intestinal Bacteria to Maximize the Effect", Bulletin of the Faculty of Agriculture, 2008, pp. 93-97, vol. 57(3), Meiji University. Partial English Translation.
Totsu et al, "Bifidobacterium and enteral feeding in preterm infants: Cluster—randomized trial", Pediatrics International, 2014, pp. 714-719, vol. 56.
Cong et al., "Gut Microbiome and Infant Health: Brain-Gut-Microbiota Axis and Host Genetic Factors", The Yale Journal of Biology and Medicine, 2016, pp. 299-308, vol. 89.
Tillisch et al., "Consumption of Fermented Milk Product With Probiotic Modulates Brain Activity", Gastroenterology: Official Publication of the American Gastroenterological Association, 2013, pp. 1394-1401, vol. 144, No. 7.

\* cited by examiner

*Primary Examiner* — Sarvamangala Devi
(74) *Attorney, Agent, or Firm* — The Webb Law Firm

(57) ABSTRACT

An object of the present invention is to provide a brain function improving agent for neonates, especially, newborn neonates. According to the present invention, there is provided a brain function improving agent for neonates, comprising a lactic acid bacterium and/or a *Bifidobacterium*. The brain function improving agent or composition for improving brain function for neonates according to the present invention is advantageous in that the use thereof can improve the developmental quotient without any side effect and also enables effective development and growth of neonates.

5 Claims, No Drawings
Specification includes a Sequence Listing.

COMPOSITION FOR IMPROVING BRAIN FUNCTION FOR NEONATES

CROSS-REFERENCE TO RELATED APPLICATIONS

This application is the United States national phase of International Application No. PCT/JP2017/014915 filed Apr. 12, 2017, and claims priority to Japanese Patent Application No. 2016-80676 filed on Apr. 13, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 8577_1806228_ST25.txt. The size of the text file is 732 bytes, and the text file was created on Oct. 10, 2018.

TECHNICAL FIELD

The present invention relates to a composition for improving brain function for neonates.

BACKGROUND ART

As humans grow after birth, appropriate development of the brain function is required in order that they adapt to and enjoy social life. The development of the brain function in adulthood requires the development of the brain function in the process of development, i.e., before adulthood.

As food products for babies and infants and for children, food products containing a functional ingredient which can be expected to improve the brain function, such as eicosapentaenoic acid (EPA) and/or docosahexaenoic acid (DHA), are currently marketed. Also, when food products not only for babies and infants and for children but also for adults and aged persons are intended, not only eicosapentaenoic acid (EPA) and/or docosahexaenoic acid (DHA) but also a number of food ingredients are known to have the effect of improving the brain function.

Further, among probiotics which exhibit functionality due to intake of a useful microorganism, an edible composition comprising *Bifidobacterium longum* ATCC BAA-9 is known to suppress the reduction in hippocampal BDNF (brain-derived neurotrophic factor) expression (Patent Document 1).

REFERENCE LIST

Patent Document

Patent Document 1: JPT 2011-517568

SUMMARY OF INVENTION

The composition of Patent Document 1 is intended to treat or prevent anxiety and related disorders of adults, and cannot be applied for improvement of the brain function including improvement in developmental quotient of babies who have underdeveloped nerves, especially newborn neonates since the effect on developed nervous tissues and the effect on developing nervous tissues cannot be equated with each other. Examples in Patent Document 1 present results of phenomena caused by infection with *Trichuris muris* using an animal test system by use of mice and phenomena caused upon administration of DSS. In other words, these results are obtained under special conditions, and it is difficult even to apply the composition to fully-developed healthy adults under normal conditions.

Since a functional material which suggests the effect of improving the adult brain function, when administered especially to newborn neonates, might affect their subsequent growth, for example, due to side effects, the development of the brain function has been promoted by improvement of living environments such as enhancement of educational coaching.

An object of the present invention is to provide a composition for improving brain function for neonates and a brain function improving agent for neonates.

Now, the present inventors have found that, upon oral feeding of a lactic acid bacterium and/or a *Bifidobacterium* to neonates, especially newborn neonates, the developmental quotient can be improved. The present invention is based on this finding.

Specifically, the present invention is as follows.

[1] A composition for improving brain function for neonates and a brain function improving agent for neonates, each comprising a lactic acid bacterium and/or a *Bifidobacterium* as active ingredient(s) (hereinafter referred to also as "the composition and agent of the present invention" in some cases).

[2] The composition and agent according to [1], wherein the active ingredient is a *Bifidobacterium*.

[3] The composition and agent according to [1] or [2], wherein the *Bifidobacterium* is *Bifidobacterium bifidum*.

[4] The composition and agent according to any one of [1] to [3], wherein the *Bifidobacterium* is the *Bifidobacterium bifidum* OLB6378 strain (Accession No. NITE BP-31).

[5] The composition and agent according to any one of [1] to [4], wherein the *Bifidobacterium* is a heat-treated bacterial cell.

[6] The composition and agent according to any one of [1] to [5], wherein the *Bifidobacterium* is continuously fed or administered in a bacterial count of $10^8$ or more per day for one month or longer.

[7] The composition and agent according to any one of [1] to [6], which is a food product.

[8] Use of a lactic acid bacterium and/or a *Bifidobacterium* for the manufacture of a composition for improving brain function for neonates or a brain function improving agent for neonates.

[9] A lactic acid bacterium and/or a *Bifidobacterium* for use in the improvement of the neonatal brain function.

[10] A method for improving the neonatal brain function, which comprises feeding or administering an effective amount of a lactic acid bacterium and/or a *Bifidobacterium* to a subject in need thereof.

According to the composition and agent of the present invention, the brain function improving effect based on the effect of improving the developmental quotient can be expected in neonates, especially newborn neonates. Since the lactic acid bacterium and/or *Bifidobacterium* as the active ingredient(s) of the present invention are/is contained in food materials which human beings have taken for many years, the composition and agent of the present invention are beneficial in that they can improve the developmental quotient without any side effect and enable effective development and growth of neonates.

DETAILED DESCRIPTION OF THE INVENTION

<Lactic Acid Bacterium>

The kind and source of the lactic acid bacterium used in the present invention are not limited. Specifically, examples of the lactic acid bacterium include the genus *Streptococcus* such as *S. thermophiles*; the genus *Lactobacillus* such as *L. bulgaricus*, *L. gasseri* and *L. acidophilus*; the genus *Lactococcus* such as *L. lactis*, *L. lactis* subsp. *cremoris* and *L. lactis* subsp. *lactis biovar. Diacetylactis*; and the genus *Leuconostoc*.

<Bifidobacterium>

The kind and source of the *Bifidobacterium* used in the present invention are not limited. Specifically, examples of the *Bifidobacterium* include Bifidobacteria such as *Bifidobacterium bifidum*, *Bifidobacterium longum*, *B. breve*, *B. adolescentis*, *B. infantis*, *B. pseudolongum* and *B. thermophilum*.

Specifically, examples of *Bifidobacterium bifidum* include the *Bifidobacterium bifidum* OLB6378 strain (Accession No. NITE BP-31), and the composition and agent of the present invention could be provided by using this strain.

The present inventors deposited this strain with NITE (National Institute of Technology and Evaluation) Patent Microorganisms Depositary (NPMD). The information identifying the deposit is as follows.

The present inventors deposited the *Bifidobacterium bifidum* OLB6378 strain (*Bifidobacterium bifidum* OLB6378) under the following conditions.
(1) Name of Depositary Institution: NITE (National Institute of Technology and Evaluation) Patent Microorganisms Depositary (NPMD)
(2) Contact: 2-5-8, Kazusakamatari, Kisarazu-shi, Chiba 292-0818 (Tel: 0438-20-5580)
(3) Accession No. NITE BP-31
(4) Indication for Identification: *Bifidobacterium bifidum* OLB6378
(5) Date of Original Deposit: Oct. 26, 2004
(6) Date of Transfer to Deposit under the Budapest Treaty: Jan. 18, 2006

The *Bifidobacterium bifidum* OLB6378 strain is a Gram-positive obligately anaerobic rod derived from feces of human babies and infants. When this strain is applied onto a BL agar medium (Eiken Chemical Co., Ltd.) flat plate to culture the strain in an anaerobic condition using Anaero-Pack-Kenki (manufactured by MITSUBISHI GAS CHEMICAL COMPANY, INC.) at 37° C. for 48 hours, an opaque, circular hemispherical, glossy colony is formed. Also, PCR products are observed in PCR using specific primers for *Bifidobacterium bifidum* (Intestinal Flora Symposium 8, Molecular Biological Detection and Identification of Intestinal Flora, Tomotari MITSUOKA & Takahiro MATSUMOTO), specifically, species-specific primers for the 16S rRNA region, i.e., BiBIF-1: CCA CAT GAT CGC ATG TGA TT (SEQ ID NO: 1) and BiBIF-2: CCG AAG GCT TGC TCC CAA A (SEQ ID NO: 2). Also, this strain has fermentative capacity for galactose, glucose, fructose, lactose and gentiobiose.

As the medium for culturing the strain of the present invention, a medium commonly used as a medium for lactic acid bacteria and/or Bifidobacteria can be used. Namely, the medium usable in the present invention is not especially limited, and any medium can be used so long as the medium contains, in addition to a main carbon source, a nitrogen source, an inorganic matter and other nutrients in amounts within predetermined ranges. Lactose, glucose, sucrose, fructose, a starch hydrolysate, blackstrap molasses or the like can be used as the carbon source according to the ability of the bacterium used to utilize and grow on the substance. Organic nitrogen-containing substances such as casein hydrolysates, whey protein hydrolysates and soybean protein hydrolysates can be used as the nitrogen source. In addition, meat extract, fish meat extract, yeast extract or the like can be used as a growth promoter.

Especially, the *Bifidobacterium* is preferably cultured under anaerobic conditions, and a known technique such as a method of culturing the bacterium while flowing a carbon gas can be applied. However, the bacterium can also be cultured by using any other technique, for example, under microaerophilic conditions in commonly-used liquid static culture or under batch culture conditions. The culture temperature ranges from 25 to 50° C., especially preferably from 35 to 42° C., but the present invention is not limited to this, and other temperature conditions may be employed so long as the bacterium can grow. The pH of the medium during culture is preferably maintained at 6.0 to 7.0, but other pH conditions may be employed so long as the bacterium can grow. The culture time is preferably 3 to 48 hours, further preferably 8 to 24 hours, especially preferably 10 to 20 hours, but other culture times may be employed so long as the bacterium can grow.

The bacterial cell obtained can be incorporated in the composition and agent of the present invention in the form of a treated product of the lactic acid bacterium and/or *Bifidobacterium* obtained by the following treatment. The treated product of the lactic acid bacterium and/or *Bifidobacterium* includes cultures remaining unchanged since the end of culture; cultures subjected to centrifugation, filtration or the like after the end of culture; concentrates of the cultures; products obtained by further processing the cultures into a pasty state; dried products (such as spray-dried products, freeze-dried products, vacuum-dried products and drum-dried products) obtained by various methods; liquid products in which the cultures are dispersed in a medium; diluted products obtained by diluting the cultures with a diluent; heat-treated products (heat-treated bacterial cell) obtained by heat treatment; light irradiation-treated products (light irradiation-treated bacterial cells) obtained by treatment with ultraviolet and/or radioactive rays; drug-treated products (drug-treated bacterial cells) obtained by treatment with a drug (bactericide, antimicrobial, bacteriostatic agent); and crushed products obtained by crushing the dried products by a mill or the like. Centrifugation, filtration and concentration are performed by commonly-used techniques. Drying can be performed, for example, through vacuum drying, spray drying, freeze drying or drum drying. These products are sometimes abbreviated herein as "treated product of the lactic acid bacterium and/or *Bifidobacterium*" or "treated product."

The lactic acid bacterium and/or *Bifidobacterium* and treated products thereof obtained by the method described above can be incorporated in the composition and agent of the present invention, as viable bacteria directly or as heat-treated and crushed or uncrushed products, alone or as a mixture of two or more species. Viable bacteria can be expected to provide, for example, the effect of proliferating in the body (in the intestine) after feeding or administration. Heat-treated bacterial cells (for example, those having a form such that no colony of the *Bifidobacterium* would be formed even when a 0.1-ml sample from a suspension (dispersion) of a heat-treated *Bifidobacterium* is smeared over a petri dish containing a medium which allows the *Bifidobacterium* to grow and cultured under anaerobic conditions) are preferred because it is not necessary to consider the property of the *Bifidobacterium* that it is hard to exist in the presence of oxygen and because the application range thereof as the composition and agent of the present invention would be expanded.

Above all, the *Bifidobacterium* is especially preferably a viable *Bifidobacterium*. It is inferred that, upon continuous feeding or administration of the viable *Bifidobacterium* to neonates in a manner as will be described later, the *Bifidobacterium* would be fixed in the intestine of the neonates and persistently provide the effect of the present invention.

As heat treatment conditions when the heat-treated *Bifidobacterium* is used in the present invention, for example, the heating temperature is normally 60 to 300° C., preferably 60 to 200° C., more preferably 60 to 150° C., further preferably 60 to 140° C., still further preferably 60 to 130° C., still further preferably 60 to 120° C., still further preferably 60 to 110° C., still further preferably 60 to 100° C., still further preferably 70 to 100° C., still further preferably 80 to 100° C., especially preferably 85 to 95° C. The heating temperature is preferably defined as 60° C. or higher as a heat treatment condition since the nutritive cells of the *Bifidobacterium* are sterilized. Also, the heating temperature is preferably defined as 300° C. or lower as a heat treatment condition since the *Bifidobacterium* does not carbonize and remains.

Further, the heat treatment time is normally 0.01 to 120 minute(s), preferably 0.015 to 60 minute(s), more preferably 0.02 to 40 minute(s), further preferably 0.025 to 30 minute(s), still further preferably 0.03 to 25 minute(s), especially preferably 0.03 to 20 minute(s). The heat treatment time is preferably defined as 0.1 minute or more since the nutritive cells of the *Bifidobacterium* are sterilized. Also, the heat treatment time is preferably defined as 120 minutes or less since heat denaturation is suppressed, thereby ensuring effective sterilization of the nutritive cells.

The optimum heat treatment time can be defined as, for example, 0.2 to 120 minute(s), preferably 0.2 to 60 minute(s), more preferably 0.2 to 40 minute(s), further preferably 0.2 to 30 minute(s), still further preferably 0.2 to 25 minute(s), especially preferably 0.2 to 20 minute(s) in the heat treatment within a low temperature range (60 to 100° C.). Also, the optimum heat treatment time is, for example, 0.01 to 0.5 minute, preferably 0.015 to 0.5 minute, more preferably 0.02 to 0.5 minute, further preferably 0.025 to 0.5 minute, still further preferably 0.03 to 0.5 minute, especially preferably 0.03 to 0.5 minute in the heat treatment within a high temperature range (100 to 300° C.). For example, the heat treatment is carried out under the conditions: at 90° C. and for 15 minutes.

The heat treatment method is not especially limited. For example, the bacterial cell obtained can be heated under predetermined conditions by use of a heat sterilizer such as a plate type sterilizing machine, a tubular type sterilizing machine, a direct heating type sterilizing machine or a jacketed tank.

In order to provide the effect of improving the neonatal brain function according to the present invention, the amount of the lactic acid bacterium and/or *Bifidobacterium* to be fed or administered is, for example, $10^8$ or more, $10^8$ to $10^{12}$, $5\times10^8$ to $5\times10^{11}$, $10^9$ to $10^{11}$, $5\times10^9$ to $5\times10^{10}$, $6\times10^9$ to $4\times10^{10}$, or $7\times10^9$ to $3\times10^{10}$ per day. The amount is preferably $8\times10^9$ to $2\times10^{10}$, further preferably $9\times10^9$ to $2\times10^{10}$ per day. This is because the brain function improving effect based on the improvement in developmental quotient of neonates can effectively be achieved by adopting an amount within the above-specified range. The composition and agent of the present invention have been found to be ingredients which provide prophylactic and therapeutic effect, namely, active ingredients, and the use purpose thereof is not limited so long as they can exert the effect.

Also, the composition and agent of the present invention have few side effects, and thus can be continuously fed or administered even to neonates, especially newborn neonates. In order to provide the effect of improving the neonatal brain function, the period for feeding or administering the lactic acid bacterium and/or *Bifidobacterium* of the present invention is, for example, 1 month or more, 1 to 12 month(s), 1 to 10 month(s), 1 to 9 month(s), 1 to 8 month(s), 2 to 7 months, from the viewpoint of the period. This is because the effect of improving the neonatal brain function can effectively be achieved by adopting a period within the above-specified range. Especially, it is preferable to continuously apply the lactic acid bacterium and/or *Bifidobacterium* in a bacterial count of $10^{10}$ or more per day for 1 month or more. From the viewpoint of the body weight of neonates, the period for feeding or administering the *Bifidobacterium* of the present invention is, for example, a period until the body weight of neonates arrives at 1.5 kg or more, a period until the body weight of neonates arrives at 1.5 to 5 kg, a period until the body weight of neonates arrives at 1.7 to 5 kg, a period until the body weight of neonates arrives at 1.8 to 5 kg, a period until the body weight of neonates arrives at 1.9 to 5 kg, a period until the body weight of neonates arrives at 2 to 5 kg, a period until the body weight of neonates arrives at 2 to 4 kg, or a period until the body weight of neonates arrives at 2 to 3 kg. This is because the effect of improving the neonatal brain function can effectively be achieved by adopting a period within the above-specified range.

As used herein, the term "neonates" refers to babies who are just newborn, and, more specifically, includes healthy neonates, premature babies, preterm babies and low birth weight babies. In the present invention, the species of the neonates include a human, unless otherwise specified.

Also, the term "neonates" refers to children in a neonatal period, and the term "neonatal period" means a period shortly after birth. In the case of a human, the neonatal period is normally within 4 weeks after birth.

It was demonstrated, as will be illustrated in the following Examples, that the composition and agent of the present invention, when started to be fed or administered to neonates, especially newborn neonates and thereafter continuously fed or administered, exhibited the brain function improving effect based on the improvement in developmental quotient. Specifically, it was demonstrated that the composition and agent of the present invention could significantly improve the developmental quotient especially for neonates having a birth weight of 1000 g or more, as compared with the case where neither of them was fed or administered. In brief, upon feeding or administration of the composition and agent of the present invention, the effect of improving the developmental quotient is imparted to newborn neonates without any side effect, and can be expected even in the subsequent growth. In other words, the inconvenience of and anxiety about life (i.e., life in which people are forced to promote the development of brain function by improvement of living environments such as enhancement of educational coaching) can be eliminated and/or alleviated.

Newborn neonates have underdeveloped neurons, and the brain function improving effect based on the improvement in developmental quotient is obtained by feeding or administering the composition and agent of the present invention each comprising a lactic acid bacterium and/or a *Bifidobacterium* as active ingredient(s) to the neonates at this time. Therefore, significant development of brain function in the subsequent growth process can be expected. Also, in addition to feeding or administration of the composition and agent of the present invention, the improvement of living environments such as enhancement of educational coaching can promote the development of brain function, and can further be expected to improve the developmental quotient. In the present invention, the term "brain function improvement" is used in a sense including the improvement in developmental quotient and the promotion or acceleration of the development of brain function. The phrase "newborn neonates" as used herein refers to neonates, for example, 0 to 60 day(s) old, 0 to 50 day(s) old, 0 to 40 day(s) old, 0 to 30 day(s) old, 0 to 20 day(s) old, 0 to 15 day(s) old or 0 to 10 day(s) old. Also, the term "low birth weight babies" as used herein refers to babies having a birth weight of 300 to 3000 g, 350 to 2900 g, 400 to 2800 g, 450 to 2700 g, 500 to 2600 g or 500 to 2500 g, in the case of humans. Further, the phrase "low birth weight babies having a birth weight of 1000 g or more" as used herein refers to babies having a birth weight of 1000 to 3000 g, 1000 to 2900 g, 1000 to 2800 g, 1000 to 2700 g, 1000 to 2600 g or 1000 to 2500 g, in the case of humans.

In the composition and agent of the present invention, the lactic acid bacterium and/or *Bifidobacterium* can be used alone or as a mixture with any other ingredient. The amount of the lactic acid bacterium and/or *Bifidobacterium* to be incorporated in the composition and agent of the present invention can be arbitrarily determined according to the purpose, intended use, form, dosage form, symptom, body weight or the like, and the lactic acid bacterium and/or *Bifidobacterium* can be incorporated in an amount of 0.1 to 90% (w/w), further preferably 0.1 to 50% based on the total weight, though the present invention is not limited thereto. This is because the composition and agent are easily fed or administered due to the fact that the amount of the lactic acid bacterium and/or *Bifidobacterium* to be incorporated therein falls within the above-specified range. In the present invention, the claimed agent can be designed to comprise a lactic acid bacterium and/or a *Bifidobacterium*, and the claimed composition can be designed to comprise a lactic acid bacterium and/or a *Bifidobacterium* and any other ingredient.

The composition and agent of the present invention can be administered either orally or parenterally (e.g., intramuscularly, subcutaneously, intravenously, as a suppository, or percutaneously). Also, the composition and agent of the present invention can be administered without being affected by side effects caused by drug administration. Especially, *Bifidobacterium bifidum* OLB6378 (NITE BP-31) of the present invention is considered to cause no side effect and to be safe, even when administered to newborn neonates (Totsu et al., (2014) PEDIATRICS INTERNATIONAL Vol. 56, No. 5, pp. 714-719). Further, the composition and agent of the present invention improve diarrhea and constipation, suppress growth of harmful bacteria in the intestine, produce vitamins B and promote digestion and absorption by lactose degradation, and, simultaneously, provides the brain function improving effect based on the improvement in developmental quotient.

Specifically, the composition and agent of the present invention can be utilized in either form of medicaments or food or beverage products. For example, the composition and agent are expected to provide the brain function improving effect, upon direct administration as medicaments or direct feeding as special-to-use foods such as foods for specified health uses or nutritional foods. Examples of the special-to-use foods and nutritional foods include formula milk, fluid diets, foods for sick persons, foods such as milk powder for infants, foods such as milk powder for lactating women, supplements and nutrient enriched foods.

When the composition and agent of the present invention are used as medicaments, examples of their form can include oral administration thereof in the form of preparations such as a tablet, a coated tablet, a capsule agent, a granule, a powder, a solution, a syrup and an emulsion. These various preparations are prepared by applying a known adjuvant which can be commonly used in the technical field of preparation of medicaments such as a dispersant, an excipient, a binder, a disintegrant, a lubricant, a colorant, a flavoring agent, a solubilizer, a suspension and a coating agent to the bacterial cell and/or treated product of the present invention, which are/is principal agent(s), in accordance with a conventional method, and can be used as the pharmaceutical composition and agent of the present invention.

The composition and agent of the present invention are preferably used as compositions comprising a dispersant mixed therewith. Examples of the dispersant include milk protein such as casein, soybean protein, peptides, amino acids, starch, dextrin, xylan, oligosaccharides, saccharides (glucose, lactose, sucrose, galactose and maltose) and sugar alcohols (trehalose, xylitol, erythritol, palatinose, trehalulose and xylose). Among these dispersants, dextrin is especially preferred. This is because a powder can be granulated by using dextrin as the dispersant and because dextrin is easy to handle, for example, in dispersion and dissolution and can also be stored for a long term.

Dextrin is preferably formed in a granular shape. This is because granular dextrin has not only high solubility but also high filling performance and thus can be divided and packaged into portions of a small amount each, and also because granular dextrin is advantageous from the viewpoint of manufacture in that it can be accurately divided and packaged, without variation in mass distribution, simply by dropping it into a packaging material therefor.

The mass ratio of the lactic acid bacterium and/or *Bifidobacterium* as the active ingredient(s) to the dispersant in the composition and agent of the present invention ranges preferably from 1:100 to 1:2, more preferably from 1:100 to 1:10, further preferably 1:100 to 1:20. This is because the active ingredient can efficiently be dispersed by defining the mass ratio within the above-specified range.

For example, in the case of oral feeding or administration of the composition and agent of the present invention each comprising the lactic acid bacterium and/or *Bifidobacterium* as the active ingredient(s) and dextrin, it is possible to divide the composition and agent into portions of a predetermined amount each, to package each of the portions in a packaging material to form a package, and then to feed or administer the composition and agent contained in the package. In the present invention, the composition and agent of the present invention are preferably divided into single-dose packages or packaged so that the amount thereof contained in a plurality of packages corresponds to a single dose, and are especially preferably divided into single-dose packages.

When the composition and agent of the present invention are added to a food composition having no side effect, they may be added to various food and beverage products (for example, cow milk, refreshing drinks, fermented milk, yogurt, cheese, bread, biscuits, crackers, pizza crusts, formula milk, fluid diets, foods for sick persons, foods such as milk powder for infants, foods such as milk powder for lactating women and nutritional foods), and such food and beverage products may be fed. The composition and agent of the present invention can be used as they are or mixed with any other food or food ingredient, i.e., can be used in accordance with a conventional method in common food compositions. Also as for their properties, they may be in any of commonly-used states of food and beverage products, for example, a solid state (powder, granule, etc.), a pasty state, a liquid state and a suspension state. The composition and agent of the present invention takes such a form and can thus be fed without causing any psychological discomfort.

Also, the composition and agent of the present invention can be used as compositions comprising side effect-free water, protein, carbohydrate, lipid, vitamin, mineral, organic acid, organic base, fruit juice, flavor or the like mixed therewith. Examples of the protein include animal and plant proteins such as whole powdered milk, skimmed milk, partially skimmed milk, casein, whey powder, whey protein, whey protein concentrate, whey protein isolate, α-casein, β-casein, κ-casein, β-lactoglobulin, α-lactalbumin, lactoferrin, soybean protein, chicken egg protein and meat protein, and hydrolysates thereof; and various milk-derived ingredients such as butter, milk mineral, cream, whey, non-protein nitrogen, sialic acid, phospholipid and lactose. All of side effect-free ingredients that have been used as medicaments or food or beverage products are applicable. Also, two or more of these ingredients can be used in combination.

Examples of the carbohydrate include saccharides, processed starches (for example, soluble starch, British starch, oxidation starch, starch esters and starch ether, in addition to dextrin) and dietary fiber. Examples of the lipid include animal oils and fats such as lard, fish oils and the like, and fractionated oils, hydrogenated oils and transesterified oils thereof; and vegetable oils and fats such as palm oil, safflower oil, corn oil, rapeseed oil and coconut oil, and fractionated oils, hydrogenated oils and transesterified oils thereof. Examples of the vitamin include vitamin A, carotenes, vitamins B, vitamin C, vitamins D, vitamin E, vitamins K, vitamin P, vitamin Q, niacin, nicotinic acid, pantothenic acid, biotin, inositol, choline and folic acid, and examples of the mineral include calcium, potassium, magnesium, sodium, copper, iron, manganese, zinc and selenium. Examples of the organic acid include malic acid, citric acid, lactic acid and tartaric acid. All of side effect-free ingredients that have been used as medicaments or food or beverage products are applicable. Also, two or more of these ingredients can be used in combination.

The composition and agent of the present invention, when provided as food products or drugs, can be manufactured by a method which is well known to those skilled in the art. Those skilled in the art can appropriately combine a step of mixing the *Bifidobacterium* or treated product of the present invention with any other ingredient, a molding step, a sterilization step, a fermentation step, a baking step, a drying step, a cooling step, a granulation step, a packaging step and the like to manufacture a desired food product or drug.

Further, the composition and agent of the present invention can be applied to foods with health claims and foods for sick persons. The system of foods with health claims was established not only for common food products but also for food products formed into a tablet, a capsule and the like in light of the domestic and international trends and the consistency with the conventional system of foods for specified health uses, and includes two types, i.e., foods for specified health uses (individually approved) and foods with nutrient function claims (complying with the specifications and standards). It is expected that the composition and agent of the present invention are directly fed as special-to-use foods (e.g., foods for specified health uses) or foods with nutrient function claims each comprising the composition and agent to provide the brain function improving effect.

Examples of the form of the composition and agent of the present invention when added to formula milk include oral compositions for brain function improvement for neonates such as formula milk for neonates, peptide milk, follow-up milk, growing-up milk, formula milk for low birth weight babies, lactose-free milk powder, low-sodium special milk powder and powder to be added to breast milk, and the form is not especially limited so long as the effect and efficacy of the present invention can be expected.

For example, when there is manufactured and provided formula milk for neonates comprising the lactic acid bacterium and/or *Bifidobacterium* according to the present invention wherein docosahexaenoic acid (DHA), eicosapentaenoic acid (EPA), arachidonic acid (ARA), cholesterol or the like, which promotes the development and growth of neonates, is incorporated in a proper amount to make its formulation close to that of breast milk, further effective development and growth of neonates can also be expected.

Also, when there is manufactured and provided formula milk for neonates comprising the lactic acid bacterium and/or *Bifidobacterium* according to the present invention with strongly allergenic β-lactoglobulin being removed or reduced, formula milk for neonates comprising the lactic acid bacterium and/or *Bifidobacterium* according to the present invention wherein a nucleoside or nucleotide having immunomodulating function is incorporated in a proper amount, or formula milk for neonates comprising the lactic acid bacterium and/or *Bifidobacterium* according to the present invention wherein soybean lecithin is not contained as an emulsifier, not only the effect of improving the neonatal brain function but also effective avoidance of neonatal allergies can be expected.

Further, when there is manufactured and provided formula milk for neonates comprising the lactic acid bacterium and/or *Bifidobacterium* according to the present invention and enriched with lactadherin having infection protecting function, or formula milk for neonates comprising the lactic acid bacterium and/or *Bifidobacterium* according to the present invention wherein at least one of fructooligosaccharide, nucleoside, nucleotide, taurine and zinc, which enhance immunity, is incorporated in a proper amount, not only the effect of improving the neonatal brain function but also effective enhancement in immunity of neonates can be expected.

Further, when there is manufactured and provided formula milk for neonates comprising the lactic acid bacterium and/or *Bifidobacterium* according to the present invention wherein β-lactoglobulin, which is hard to digest and absorb, is selectively degraded, or formula milk for neonates comprising the lactic acid bacterium and/or *Bifidobacterium* according to the present invention and enriched with highly digestible α-lactalbumin, not only the effect of improving the neonatal brain function but also effective improvement in digestion and absorption in the digestive tract of neonates can be expected.

Further, when there is manufactured and provided formula milk for neonates comprising the lactic acid bacterium and/or *Bifidobacterium* according to the present invention wherein fructooligosaccharide, nucleoside or nucleotide, which promotes the formation of appropriate intestinal bacterial flora, is incorporated in a proper amount, or formula milk for neonates comprising the lactic acid bacterium and/or *Bifidobacterium* according to the present invention wherein lactose, which promotes the formation of appropriate intestinal bacterial flora, is incorporated in a proper amount, not only the effect of improving the neonatal brain function but also effective improvement in feces properties of neonates can be expected.

The lactic acid bacterium and/or *Bifidobacterium* as the active ingredient(s) of the present invention may be used as additive(s) to pharmaceutical compositions, food and beverage products which have been eaten and can be expected to have few side effects, or compositions which can be expected to provide the brain function improving effect including the effect of improving the developmental quotient, and can be fed or administered orally or through a tube.

The lactic acid bacterium and/or *Bifidobacterium* as the active ingredient(s) of the present invention have/has the excellent effects and efficacies as described above not only on a human but also on mammals except a human. Therefore, according to the present invention, there are provided a feed and a feed additive, especially a milk powder and a milk powder additive for feeding mammals, each which comprise a lactic acid bacterium and/or a *Bifidobacterium* as active ingredient(s).

The "developmental quotient" as referred to in the present invention is one of methods for evaluating the psychomotor development, and was demonstrated in Kyoto Scale of Psychological Development 2001. Specifically, this method is intended to calculate the developmental quotient by observing, in a predetermined set test scene, the activities and reactions of neonates to whom samples to be tested, such as the composition and agent of the present invention, were fed or administered, at the time when the neonates reached the age of 1.5. In detail, this method involves observing the postural-motor (P-M), cognitive-adaptive (C-A) and language-social (L-S) domains to derive the developmental ages and developmental quotients in all the domains. That is, the proportion (percent) of the developmental age obtained by the test to the actual age corresponds to developmental quotient, and it is understood that, for example, when the developmental quotient is 100, the developmental age and the actual age are equivalent to each other. Incidentally, the method for evaluating the psychomotor development described above includes various techniques, and, even if the effect obtained is equivalent to the improvement in developmental quotient demonstrated in Kyoto Scale of Psychological Development 2001 when the development of neonates is verified by a method other than Kyoto Scale of Psychological Development 2001, the effect has the same meaning as the improvement in developmental quotient referred to in the present invention.

According to the present invention, there is provided a method for improving the neonatal brain function, which comprises feeding or administering an effective amount of a lactic acid bacterium and/or a *Bifidobacterium* or a composition comprising the lactic acid bacterium and/or *Bifidobacterium* to a subject in need thereof. The subjects for feeding or administration are neonates of mammals including a human, preferably human neonates. The method of the present invention can be carried out in accordance with the description for the composition and agent of the present invention.

Also, according to the present invention, there is provided use of a lactic acid bacterium and/or a *Bifidobacterium* or a composition comprising the lactic acid bacterium and/or *Bifidobacterium*, for the manufacture of a composition for improving brain function for neonates. Further, according to the present invention, there is provided use of a lactic acid bacterium and/or a *Bifidobacterium* or a composition comprising the lactic acid bacterium and/or *Bifidobacterium*, for the manufacture of a brain function improving agent for neonates. Furthermore, according to the present invention, there is provided use of a lactic acid bacterium and/or a *Bifidobacterium* or a composition comprising the lactic acid bacterium and/or *Bifidobacterium*, for the improvement of brain function for neonates. Furthermore, according to the present invention, there is provided a lactic acid bacterium and/or *Bifidobacterium* or a composition comprising the lactic acid bacterium and/or *Bifidobacterium* for use in the improvement of the neonatal brain function. The use of the present invention as well as the lactic acid bacterium, the *Bifidobacterium*, and the composition of the present invention can be carried out in accordance with the description for the composition and agent of the present invention.

EXAMPLES

Hereinafter, the present invention will be described in detail by way of the following examples, but is not limited thereto.

Example 1: Preparation of Test Food and Control Food

One hundred twenty (120) g of an original bacterial powder (count of viable bacteria: $3.9 \times 10^{11}$ cfu/g, trade name: "Meiji Bifipure (registered trademark)," Meiji Food Materia Co., Ltd.) of the *Bifidobacterium bifidum* OLB6378 strain (Accession No. NITE BP-31) and 2880 g of granular dextrin (Matsutani Chemical Industry Co., Ltd.) were uniformly mixed together, and a mixture was divided and packaged in portions of 1 g each to prepare a test food (viable bacteria).

In place of the test food, 3000 g of granular dextrin (Matsutani Chemical Industry Co., Ltd.) was divided and packaged in portions of 1 g each to prepare a control food (placebo).

Test Example 1

In Test Example 1, a group of subjects who took the test food (viable bacteria) was defined as a "test food (viable bacteria) intake group," and a group of subjects who took the control food (placebo) was defined as a "control food (placebo) intake group." Neonates (88 subjects having a birth weight of 1000 g or more and 80 subjects having a birth weight of less than 1000 g) were selected as the respective subject groups. Then, 89 subjects (49 subjects having a birth weight of 1000 g or more and 40 subjects having a birth weight of less than 1000 g) were selected from the test food (viable bacteria) intake group, and 79 subjects (39 subjects having a birth weight of 1000 g or more and 40 subjects having a birth weight of less than 1000 g) were selected from the control food (placebo) intake group. Each of the groups took the test food (viable bacteria) or control food (placebo) once a day. The feeding period is until the day when the body weight of the neonates arrived at 2 kg.

Test Example 2

At the time when the 89 subjects selected from the test food (viable bacteria) intake group and the 79 subjects selected from the control food (placebo) intake group in Test Example 1 each reached the age of 1.5, Kyoto Scale of Psychological Development 2001 was used to confirm their developmental quotient by an applicable test method as appropriate. Specifically, the postural-motor (P-M), cognitive-adaptive (C-A) and language-social (L-S) domains were observed to derive the developmental ages and developmental quotients in all the domains from the comprehensive viewpoint. The percent of the developmental age obtained to the actual age represents the developmental quotient, and was classified into less than 70, 70 or more and less than 85, 85 or more and less than 100, and 100 or more.

Among the 89 subjects in the test food (viable bacteria) intake group, 12 subjects showed a developmental quotient of less than 70; 12 subjects showed a developmental quotient of 70 or more and less than 85; 25 subjects showed a developmental quotient of 85 or more and less than 100; and 40 subjects showed a developmental quotient of 100 or more. In other words, in the test food (viable bacteria) intake group (89 subjects), the proportion of the developmental quotient of less than 70 was 13%; the proportion of the developmental quotient of 70 or more and less than 85 was 13%; the proportion of the developmental quotient of 85 or more and less than 100 was 28%; and the proportion of the developmental quotient of 100 or more was 45%.

On the other hand, among the 79 subjects in the control food (placebo) intake group, 15 subjects showed a developmental quotient of less than 70; 17 subjects showed a developmental quotient of 70 or more and less than 85; 23 subjects showed a developmental quotient of 85 or more and less than 100; and 24 subjects showed a developmental quotient of 100 or more. In other words, in the control food (placebo) intake group (subject 79 subjects), the proportion of the developmental quotient of less than 70 was 19%; the proportion of the developmental quotient of 70 or more and less than 85 was 22%; the proportion of the developmental quotient of 85 or more and less than 100 was 29%; and the proportion of the developmental quotient of 100 or more was 30%.

When U test was conducted between the test food (viable bacteria) intake group and the control food (placebo) intake group, the result was P=0.038. A significant difference was found between the two groups.

In view of the above, it was found that the developmental quotients of the neonates at the age of 1.5 were significantly improved by feeding or administering the composition and agent of the present invention to the neonates for a predetermined period.

Next, the developmental quotients obtained were recounted for the subjects having a birth weight of 1000 g or more (test food (viable bacteria) intake group: 49 subjects and control food (placebo) intake group: 39 subjects) in the two groups.

Among the 49 subjects in the test food (viable bacteria) intake group, 3 subjects showed a developmental quotient of less than 70; 6 subjects showed a developmental quotient of 70 or more and less than 85; 10 subjects showed a developmental quotient of 85 or more and less than 100; and 30 subjects showed a developmental quotient of 100 or more. In other words, in the test food (viable bacteria) intake group (subject 49 neonates), the proportion of the developmental quotient of less than 70 was 6%; the proportion of the developmental quotient of 70 or more and less than 85 was 12%; the proportion of the developmental quotient of 85 or more and less than 100 was 20%; and the proportion of the developmental quotient of 100 or more was 61%.

On the other hand, among the 39 subjects in the control food (placebo) intake group, 9 subjects showed a developmental quotient of less than 70; 6 subjects showed a developmental quotient of 70 or more and less than 85; 10 subjects showed a developmental quotient of 85 or more and less than 100; and 14 subjects showed a developmental quotient of 100 or more. In other words, in the control food (placebo) intake group (subject 39 neonates), the proportion of the developmental quotient of less than 70 was 23%; the proportion of the developmental quotient of 70 or more and less than 85 was 15%; the proportion of the developmental quotient of 85 or more and less than 100 was 26%; and the proportion of the developmental quotient of 100 or more was 35%.

When U test was conducted between the test food (viable bacteria) intake group and the control food (placebo) intake group, the result was P=0.009. A significant difference was found between the two groups.

In view of the above, it was found that the developmental quotients of, especially, the neonates having a birth weight of 1000 g or more, at the age of 1.5, were significantly improved by feeding or administering the composition and agent of the present invention to the neonates for a predetermined period.

The invention claimed is:

1. A method of improving neaonatal brain function comprising:
   feeding or orally administering an effective amount of *Bifidobacterium bifidum* cells to a neonatal subject in need thereof and
   evaluating the psychomotor development of the subject by determining the subject's developmental age and developmental quotients,
   wherein the *Bifidobacterium bifidum* cells are viable cells of the *Bifidobacterium bifidum* OLB6378 strain having the accession number NITE BP-31.

2. The method of claim 1, wherein the neonatal subject has a birth weight of 1000 grams or more.

3. The method of claim 1, wherein the effective amount is $9 \times 10^8$ or $2 \times 10^{10}$ of the *Bifidobacterium bifidum* cells fed per day.

4. The method of claim 1, wherein the *Bifidobacterium bifidum* cells are provided in the form of a food product.

5. The method of claim 1, wherein $10^8$ or more of the *Bifidobacterium bifidum* cells are continuously fed per day for one month or longer.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ccacatgatc gcatgtgatt                    20

<210> SEQ ID NO 2
<211> LENGTH: 19
<212> TYPE: DNA
<213> ORGANISM: Artificial Sequence
<220> FEATURE:

```
<223> OTHER INFORMATION: PCR primer

<400> SEQUENCE: 2
ccgaaggctt gctcccaaa                                                    19
```